(12) United States Patent
Reimers et al.

(10) Patent No.: US 6,302,204 B1
(45) Date of Patent: Oct. 16, 2001

(54) METHOD OF OBTAINING IMPROVED GEOPHYSICAL INFORMATION ABOUT EARTH FORMATIONS

(75) Inventors: Nils Reimers, Stavanger (NO); John W. Harrell, Spring; Paulo S. Tubel, The Woodlands, both of TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/604,138

(22) Filed: Jun. 27, 2000

Related U.S. Application Data

(62) Division of application No. 09/532,466, filed on Mar. 22, 2000, now Pat. No. 6,209,640, which is a division of application No. 08/948,150, filed on Oct. 9, 1997, now Pat. No. 6,065,538, which is a continuation-in-part of application No. 08/856,656, filed on May 15, 1997, now Pat. No. 6,006,832, which is a continuation-in-part of application No. 08/695,450, filed on Aug. 12, 1996, now Pat. No. 5,662,165, which is a division of application No. 08/526,827, filed on Sep. 11, 1995, now Pat. No. 5,730,219, which is a continuation-in-part of application No. 08/386,480, filed on Feb. 9, 1995, now Pat. No. 5,597,042

(60) Provisional application No. 60/027,860, filed on Oct. 9, 1996, and provisional application No. 60/045,354, filed on May 2, 1997.

(51) Int. Cl.[7] .................................................. E21B 47/00
(52) U.S. Cl. ................. 166/250.03; 166/402; 166/272.2; 166/373; 367/39; 367/57; 181/112; 340/853.1
(58) Field of Search .......................... 166/250.01, 250.03, 166/401, 402, 272.2, 271, 269, 273; 73/589, 592, 598; 340/856.1, 853.1; 181/108, 112; 367/37–39, 56, 57

(56) References Cited

U.S. PATENT DOCUMENTS

Re. 32,463  7/1987  Westlake et al. ...................... 175/48
Re. 33,690  9/1991  Adams, Jr. et al. ................... 166/53
Re. 34,111  10/1992  Wynn ..................................... 166/53

(List continued on next page.)

FOREIGN PATENT DOCUMENTS

| 0200535A2 | 11/1986 | (EP) . |
| 0200535B1 | 11/1986 | (EP) . |
| 0295178A2 | 12/1988 | (EP) . |

OTHER PUBLICATIONS

Crosswell Seismic Radial Survey Tomograms and the 3–D Interpretation of a Heavy Oil Steamflood, Geophysics, vol. 60, No. 3, (May–Jun. 1995), pp. 651–659.

*Primary Examiner*—Roger Schoeppel
(74) *Attorney, Agent, or Firm*—Madan, Mossman & Sriram, P.C.

(57) ABSTRACT

The present invention provides a method for forming wellbores. In one method, one or more wellbores are drilled along preplanned paths based in part upon seismic surveys performed from the surface. An acoustic transmitter conveyed in such wellbores transmits acoustic signals at a one or more frequencies within a range of frequencies at a plurality of spaced locations. A plurality of substantially serially spaced receivers in the wellbores and/or at surface receive signals reflected by the subsurface formations. The sensors may be permanently installed in the boreholes and could be fiber optic devices. The receiver signals are processed by conventional geophysical processing methods to obtain information about the subsurface formations. This information is utilized to update any prior seismographs to obtain higher resolution seismographs. The improved seismographs are then used to determine the profiles of the production wellbores to be drilled. Borehole seismic imaging may then be used to further improve the seismographs and to plan future wellbores. Crosswell tomography may be utilized to further update the seismographs to manage the reservoirs. The permanently installed sensors may also be used to monitor the progress of fracturing in nearby wells and thereby provide the necessary information for controlling fracturing operations.

22 Claims, 6 Drawing Sheets

U.S. PATENT DOCUMENTS

| | | | |
|---|---|---|---|
| 3,219,107 | 11/1965 | Brown, Jr. et al. . | |
| 3,357,490 | 12/1967 | Holmes | 166/53 |
| 3,697,952 | 10/1972 | Hayre | 340/147 R |
| 3,731,742 | 5/1973 | Sizer et al. | 166/315 |
| 3,958,633 | 5/1976 | Britch et al. | 166/117.5 |
| 4,105,279 | 8/1978 | Glotin et al. | 339/117 R |
| 4,125,163 | 11/1978 | Fitzpatrick | 166/314 |
| 4,150,721 | 4/1979 | Norwood | 166/53 |
| 4,337,653 | 7/1982 | Chauffe | 73/151 |
| 4,413,676 | 11/1983 | Kervin | 166/53 |
| 4,475,386 | 10/1984 | Fitch et al. | 73/151 |
| 4,479,204 * | 10/1984 | Silverman . | |
| 4,524,434 | 6/1985 | Silverman | 367/37 |
| 4,581,613 | 4/1986 | Ward et al. | 340/856 |
| 4,616,700 | 10/1986 | Wood et al. | 166/250 |
| 4,622,635 | 11/1986 | Chandra et al. | 364/422 |
| 4,624,309 | 11/1986 | Schnatzmeyer | 166/66 |
| 4,633,954 | 1/1987 | Dixon et al. | 166/372 |
| 4,636,934 | 1/1987 | Schwendemann et al. | 364/132 |
| 4,664,602 | 5/1987 | Gordon | 417/56 |
| 4,685,522 | 8/1987 | Dixon et al. | 166/372 |
| 4,707,812 * | 11/1987 | Martinez . | |
| 4,712,613 | 12/1987 | Nieuwstad | 166/53 |
| 4,757,314 | 7/1988 | Aubin et al. | 340/856 |
| 4,788,545 | 11/1988 | Farque | 340/856 |
| 4,790,380 | 12/1988 | Ireland et al. | 166/250 |
| 4,796,699 | 1/1989 | Upchurch | 166/250 |
| 4,856,595 | 8/1989 | Upchurch | 166/374 |
| 4,886,126 | 12/1989 | Yates, Jr. | 175/4.54 |
| 4,896,722 | 1/1990 | Upchurch | 166/250 |
| 4,915,168 | 4/1990 | Upchurch | 166/250 |
| 4,921,048 | 5/1990 | Crow et al. | 166/372 |
| 4,922,423 | 5/1990 | Koomey et al. | 364/422 |
| 4,949,575 | 8/1990 | Rasmus | 73/152 |
| 4,969,130 | 11/1990 | Wason et al. | 367/73 |
| 4,971,160 | 11/1990 | Upchurch | 175/4.54 |
| 4,989,671 | 2/1991 | Lamp | 166/53 |
| 5,050,675 | 9/1991 | Upchurch | 166/250 |
| 5,062,084 * | 10/1991 | Schoepf et al. . | |
| 5,127,477 | 7/1992 | Schultz | 340/856 |
| 5,130,705 | 7/1992 | Allen et al. | 340/853.9 |
| 5,132,904 | 7/1992 | Lamp | 364/422 |
| 5,147,559 | 9/1992 | Brophey et al. | 210/744 |
| 5,172,717 | 12/1992 | Boyle et al. | 137/155 |
| 5,188,183 | 2/1993 | Hopmann et al. | 166/387 |
| 5,191,937 | 3/1993 | Cook, Sr. | 166/363 |
| 5,226,494 | 7/1993 | Rubbo et al. | 166/250 |
| 5,234,057 | 8/1993 | Schultz et al. | 166/319 |
| 5,259,452 | 11/1993 | Wittrisch | 166/250 |
| 5,265,677 | 11/1993 | Schultz | 166/302 |
| 5,273,112 | 12/1993 | Schultz | 166/374 |
| 5,273,113 | 12/1993 | Schultz | 166/250 |
| 5,279,363 | 1/1994 | Schultz et al. | 166/53 |
| 5,293,937 | 3/1994 | Schultz et al. | 166/250 |
| 5,318,129 * | 6/1994 | Wittrisch . | |
| 5,318,130 | 6/1994 | Manke | 166/373 |
| 5,332,035 | 7/1994 | Schultz et al. | 166/53 |
| 5,332,048 | 7/1994 | Underwood et al. | 175/26 |
| 5,343,963 | 9/1994 | Bouldin et al. | 175/27 |
| 5,353,873 | 10/1994 | Cooke, Jr. | 166/253 |
| 5,358,035 | 10/1994 | Grudzinski | 166/53 |
| 5,413,174 | 5/1995 | Schmidt | 166/250 |
| 5,457,988 | 10/1995 | Delatorre | 73/151 |
| 5,461,594 | 10/1995 | Mougenot et al. | 367/48 |
| 5,467,823 | 11/1995 | Babour et al. | 166/250.01 |
| 5,505,259 | 4/1996 | Wittrisch et al. | 166/250.01 |
| 5,586,082 | 12/1996 | Anderson et al. | 367/73 |
| 5,597,042 | 1/1997 | Tubel et al. | 166/250.01 |
| 5,662,165 | 9/1997 | Tubel et al. | 166/250.01 |
| 5,706,194 | 1/1998 | Neff et al. | 364/421 |

FOREIGN PATENT DOCUMENTS

| | | |
|---|---|---|
| 0295178A3 | 12/1988 | (EP) . |
| 0295178B1 | 12/1988 | (EP) . |
| 0547961A1 | 6/1993 | (EP) . |
| 0736666A2 | 10/1996 | (EP) . |
| 0780701A1 | 6/1997 | (EP) . |
| 2256736A | 12/1992 | (GB) . |
| WO96/21165 | 11/1996 | (WO) . |

* cited by examiner

METHOD OF OBTAINING IMPROVED GEOPHYSICAL INFORMATION ABOUT EARTH FORMATIONS

CROSS REFERENCE TO RELATED APPLICATIONS

This application is a Divisional application from U.S. patent application Ser. No. 09/532,466 filed on Mar. 22, 2000, (now U.S. Pat. No. 6,209,640) which is a Divisional application from U.S. patent application Ser. No. 08/948,150 filed on Oct. 9, 1997 (now U.S. Pat. No. 6,065,538) which is continuation in part of U.S. patent application Ser. No. 08/856,656 filed on May 15, 1997, (now U.S. Pat. No. 6,006,832 ) which is a continuation in part of patent application Ser. No. 08/695,450 filed Aug. 12, 1996 (now U.S. Pat. No. 5,662,165, issued Sep. 2, 1997) which is a divisional of patent application Ser. No. 08/526,827 filed on Sep. 11, 1995 (now U.S. Pat. No. 5,730,219) which is a continuation in part of patent application Ser. No. 08/386,480 filed Feb. 9, 1995 (now U.S. Pat. No. 5,597,042). The parent application Ser. No. 08/948,150 claimed a priority date of Oct. 9, 1996, based on Provisional Application Ser. No. 60/027,860, filed on Oct. 9, 1996 and a priority date of May 2, 1997 based on Provisional Application Ser. No. 60/045,354.

FIELD OF THE INVENTION

This invention relates generally to the placement of wellbores and management of the corresponding reservoirs and more particularly to selectively drilling one or more wellbores for conducting seismic surveys therefrom to improve the seismographs and utilizing the improved seismographs to determine the type and course of wellbores for developing a field. The method of the present invention further relates to obtaining seismic information during drilling of the wellbores and during production of hydrocarbons for improving hydrocarbon production from the reservoirs. The method of the present invention further relates to using the derived seismic information for automatically controlling petroleum production wells downhole computerized control systems.

BACKGROUND OF THE INVENTION

Seismic surveys are performed from surface locations to obtain maps of the structure of subsurface formations. These surveys are in the form of maps (referred herein as seismographs") depicting cross-section of the earth below the surveyed region or area. Three dimensional ("3D") surveys have become common over the last decade and provide significantly better information of the subsurface formations compared to the previously available two-dimension ("2D") surveys. The 3D surveys have significantly reduced the number of dry wellbores. Still, since such seismic surveys are performed from the surface, they lose resolution due to the distance between the surface and the desired hydrocarbon-bearing formations, dips in and around the subsurface formations, bed boundary delineations, which is typically several thousand feet.

Surface seismic surveys utilize relatively low frequency acoustic signals to perform such surveys because such signals penetrate to greater depths. However, low frequency signals-provide lower resolution, which provides low resolution seismographs. High frequency signals provide relatively high resolution boundary delineations, but attenuate relatively quickly and are, thus, not used for performing seismic surveys from the surface.

Only rarely would an oil company drill a wellbore without first studying the seismographs for the area. The number of wellbores and the path of each wellbore is typically planned based on the seismographs of the area. Due to the relatively low resolution of such seismographs, wellbores are frequently not drilled along the most effective wellpaths. It is therefore desirable to obtain improved seismographs prior to drilling production wellbores. Additionally, more and more complex wellbores are now being drilled, the placement of which can be improved with high definition seismographs. Furthermore, relatively recently, it has been proposed to drill wellbores along contoured paths through and/or around subsurface formations to increase potential recovery or to improve production rates of hydrocarbons. In such cases, it is even more critical to have seismographs that relatively accurately depict the delineation of subsurface formations.

Conventionally, seismographs have been updated by (a) performing borehole imaging, which is typically conducted while drilling a wellbore and (b) by cross-well tomography, which is conducted while between a number of producing wells in a region. In the case of borehole imaging, a seismic source seismic source generates acoustic signals during drilling of the wellbore. A number of receivers placed on the surface receive acoustic reflections from subsurface formation boundaries, which signals are processed to obtain more accurate bed boundary information about the borehole. This technique helps improve the surface seismographs in piecemeal basis. Data from each such well being drilled is utilized to continually update the seismographs. However, such wellbores are neither planned nor optimally placed for the purpose of conducting subsurface seismic surveys. Their wellpaths and sizes are determined based upon potential recovery of hydrocarbons. In the case of crosswell tomography, acoustic signals are transmitted between various transmitters and receivers placed in producing wellbores. The effectiveness of such techniques are reduced if the wellbores are not optimally placed in the field. Such techniques would benefit from wellbores which are planned based on improved seismographs.

In the control of producing reservoirs, it would be useful to have information about the condition of the reservoir away from the borehole. Crosswell techniques are available to give this kind of information. In seismic tomography, a series of 3-D images of the reservoir is developed to give a 4-D model or the reservoir. Such data has usually been obtained using wireline methods in which seismic sensors are lowered into a borehole devoted solely for monitoring purposes. To use such data on a large scale would require a large number of wells devoted solely to monitoring purposes. Furthermore, seismic data acquired in different wireline runs commonly suffers from a data mismatch problem where, due to differences in the coupling of the sensors to the formation, data do not match.

The present invention addresses the above-noted problems and provides a method of conducting subsurface seismic surveys from one or more wellbores. These wellbores may be drilled for the purpose of conducting such surveys. Alternatively, permanently implanted sensors in a borehole that could even be a production well could be used to gather such data. The data from such subsurface surveys is utilized to improve the previously available seismographs. The improved seismographs are then utilized to plan the production wellbores. Borehole seismic imaging and cross-well tomography can be utilized to further improve the seismographs for reservoir management and control.

SUMMARY OF THE INVENTION

The present invention provides a method for forming wellbores. In one method, one or more wellbores are drilled along preplanned paths based in part upon seismic surveys performed from the surface. An acoustic transmitter transmits acoustic signals at one or more frequencies within a range of frequencies at a plurality of spaced locations. A plurality of substantially serially-spaced receivers in the wellbores and/or at surface receive signals reflected by the subsurface formations. While the acoustic receivers are permanently deployed downhole, the acoustic transmitter may optionally be positioned permanently or temporarily downhole; or may be positioned permanently or temporarily at the surface of the well. The receiver signals are processed by conventional geophysical processing methods to obtain information about the subsurface formations. This information is utilized to update any prior seismographs to obtain higher resolution seismographs. The improved seismographs are then used to determine the profiles of the production wellbores to be drilled. Borehole seismic imaging may then be used to further improve the seismographs and to plan future wellbores. Information gathered from tomographic surveys carried out over a period of time can be used to map changes in the reservoir conditions away from the boreholes and appropriate control measures may be taken. Fiber optic sensors, along with a light source, can also be used to detect the acoustic and seismic signals.

Another embodiment of the present invention includes permanent downhole formation evaluation sensors which remain downhole throughout production operations. These formation evaluation sensors for formation measurements may include, for example, gamma ray detection liar formation evaluation, neutron porosity, resistivity, acoustic sensors and pulse neutron which can, in real time, sense and evaluate formation parameters including important information regarding water migrating from different zones. Permanently installed fiber optic sensors can also be used to measure acoustic signals, pressure, temperature and fluid flow. These are utilized to in the seismic mapping as well as in obtaining and upodating reservoir models and in managing the production of hydrocarbons.

On particularly advantageous permanent downhole sensor installation involves the permanent placement of acoustic transmitters and receivers downhole in oil, gas or injection wells for collecting real time seismic data. This seismic data is used for, among other purposes, (a) defining the reservoir; (b) defining distribution of oil, water and gas in a reservoir with respect to time; (c) monitoring the saturation, depletion and movement of oil, water and gas; and (d) monitoring the progress of a fracturing operation. In contrast to prior art seismic monitoring, the data obtained by the present invention is real time.

BRIEF DESCRIPTION OF THE DRAWINGS

For detailed understanding of the present invention, references should be made to the following detailed description of the preferred embodiment, taken in conjunction with the accompanying drawings, in which like elements have been given like numerals, wherein.

DETAILED DESCRIPTION OF THE REFERRED EMBODIMENTS

In general, the present invention provides methods for obtaining improved seismic models prior to drilling production wellbores, drilling wellbores based at least partially on the improved seismic models and method for improving reservoir modeling by continued seismic survey during the life of the production wellbores.

Figure 1:
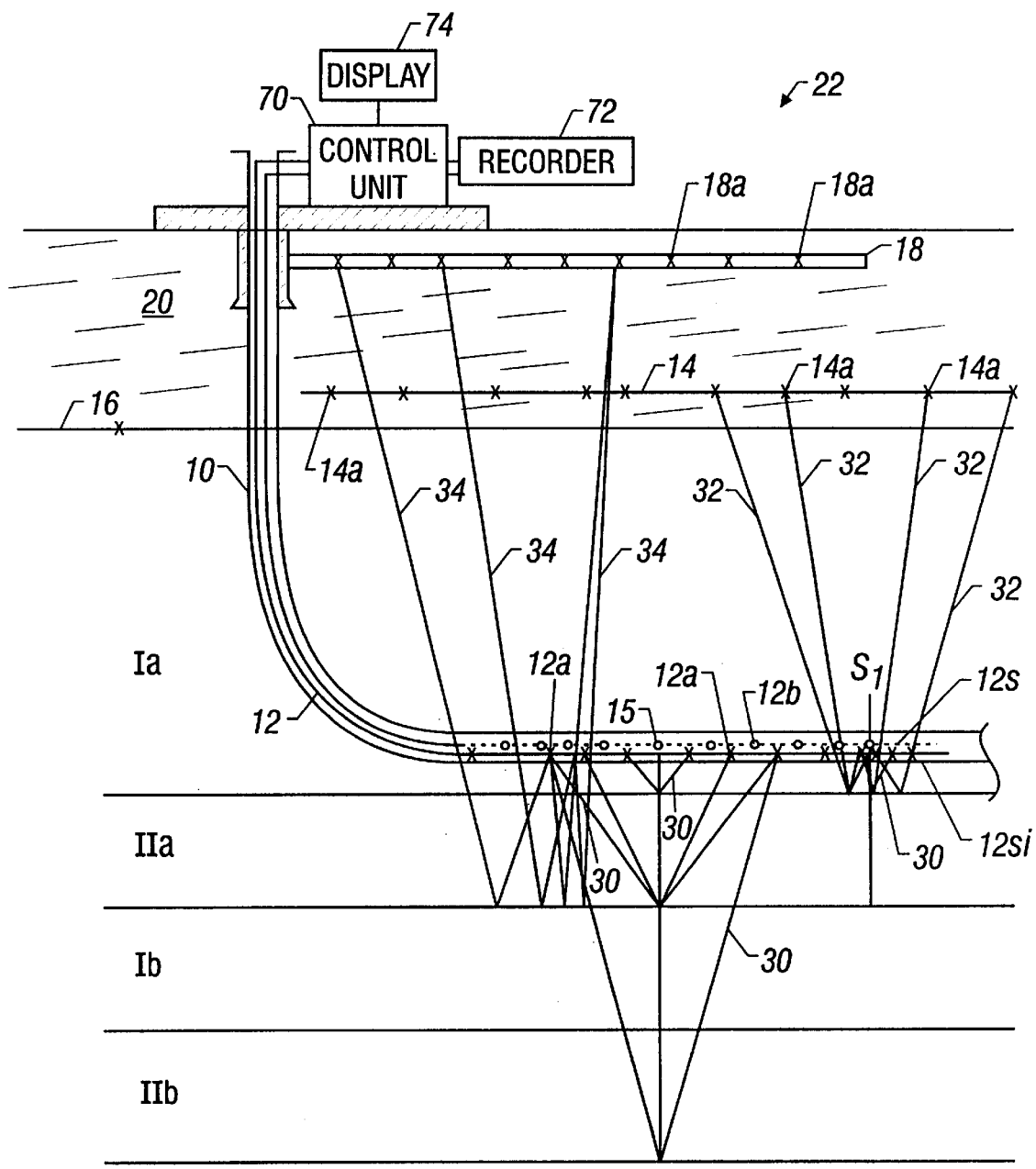
FIG. 1 shows a schematic illustration of the placement of a wellbore and corresponding transmitters and receivers for conducting subsurface seismic surveys according to an embodiment of the present invention.

FIG. 1 shows a schematic illustration of an example of the placement of a survey wellbore and receivers and the source points for conducting subsurface seismic surveys according to the present invention. For the purposes of illustration and ease of understanding, the methods of the present invention are described by way of examples and, thus, such examples shall not be construed as limitations. Further, the methods are described in reference to drilling wellbores offshore but are equally applicable to drilling of wellbores from onshore locations. In this configuration, a survey wellbore 10 is planned based on any preexisting information about the subsurface formation structure. Such information typically includes seismic surveys performed at the surface and may include information from wellbores previously formed in the same or nearby fields. As an example, FIG. 1 shows non-hydrocarbon bearing formations Ia and Ib separated by hydrocarbon bearing formations IIa and IIb (also referred to herein as the "production zones" or "reservoirs"). After the wellpath for the survey wellbore 10 has been determined, it is drilled by any conventional manner. Typically, reservoirs are found several thousand feet deep from the earth's surface and in many instances oil and gas is trapped in multiple zones separated by non-hydrocarbon bearing zones. It is preferred that the hydrocarbon bearing formations be not invaded by drilling fluids and other drilling activity except as may be necessary to drill wellbores for recovering hydrocarbons from such formations. Therefore, it is generally preferred that the survey wellbore 10 be placed in a non-hydrocarbon bearing formation, such as formation Ia. Additionally, it is preferred that the survey wellbore be placed relatively close to and along the reservoirs.

Typically, production wellbores are relatively large in diameter, generally greater than seven inches (7") in diameter. Such large diameter wellbores are expensive to drill. Survey wellbores, such as exemplary wellbore 10, however, need only be large enough to accommodate acoustic receivers, such as hydrophones, fiber optic sensors, and an acoustic source moved within the wellbore as more fully explained later. Such small diameter wellbores can be drilled relatively inexpensively in non-producing zones without concerning invading formations near the borehole. Additionally, relatively inexpensive fluids may be utilized to drill such wellbores. As noted earlier, reservoirs typically lie several thousand feet below the earth's surface and thus the survey wellbore, such as wellbore 10, may be placed several thousand feet below the earth's surface. Additionally, if the survey wellbore is not eventually going to be utilized for purposes that would require casing or otherwise completing the wellbore, such wellbore may be filled with a heavy fluid (called the "kill-weight" fluid) to prevent collapse of the wellbore.

Figure 1A:
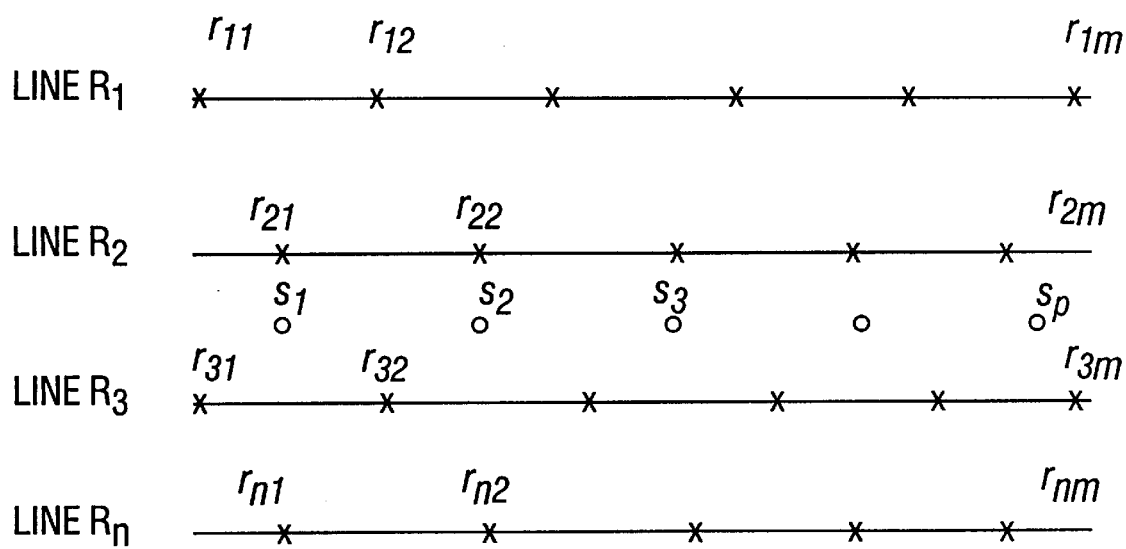
FIG. 1a shows a receiver grid for use at the surface according to an embodiment of the present invention.

Once the survey wellbore 10 has been drilled, a receiver string or line 12 with a plurality of serially spaced receivers 12a is placed along the wellbore. The receiver locations 12a are preferably equi-spaced and each receiver location 12a may include one or more receivers, such as hydrophones, seismometers or accelerometers. The receivers could also be single or a plurality of fiber optic strings or segment, each such segment containing a plurality of spaced apart fiber optic sensors: in such a case, a light source and detector (not shown) are disposed used in the wellbore to transmit light energy to the sensors and receiver the reflected light energy from the sensors and a suitably placed data acquisition and processing unit is used for processing the light signals. The use of such receiver lines is known in the art and is not described in detail herein. Alternatively or in addition to the receiver string 12, one or more receiver lines, such as lines 14, each having a plurality of serially spaced acoustic sensors 14a may be placed on the ocean bottom 16 for relatively shallow water applications. For relatively deep water applications, one or more receiver lines may be placed a relatively short distance below the water surface 22. Receiver lines 22 are made buoyant so that they remain at a desired distance below the water surface. FIG. 1a shows a plan view of an exemplary 13 configuration of a plurality of receiver lines R1–Rn that may be placed on the earth's surface. The receivers in each line designated by $r_{ij}$, where i represents the line and j represents the sequential position in the line i. The receivers in adjacent lines are shown staggered one half the distance between adjacent receivers.

The same fiber-optic sensor could be used as an acoustic sensor and to determine other downhole conditions, such as the temperature, pressure and fluid flow. The use of fiber optic sensors in downhole tools is fully described in Provisional Application Ser. No. 60/045,354, incorporated herein by reference.

Referring back to FIG. 1, to perform a seismic survey from the survey wellbore 10, a seismic source (acoustic transmitter) is energized at a first location, such as location 12$s_1$. The acoustic signals travel around the survey wellbore 10 and are reflected and refracted by the bed boundaries between the various formations. The reflected waves, such as waves 30 are detected by the receivers 12s in the survey wellbore 12. The detected signals are transmitted to a surface control unit 70, which processes the detected signals according to known seismic processing methods. Desired information relating to the survey activity is displayed on the display and any desired information is recorded by the recorder. The control unit preferably includes a computer with a seismic data processing programs for performing processing receiver data and for controlling the operation of the source 15.

The source 15 is then moved to the next location in the wellbore 10 and the above process is repeated. When receiver lines, such as lines 14 are deployed on the sea bottom 16, then the signals 32 reflected from the subsurface formations are detected by the receivers 14a. The signals detected by the sensors 14a are then collected and processed by the control unit 70 in the manner described earlier. When receiver lines 18 are suspended in the ocean water 20 then reflected signals as shown by lines 34 are detected by the receivers 18a in lines 18. The signals received by the lines 18 are then processed by the control unit 70 in the manner described earlier. It should be noted that for the purpose of this embodiment of the invention any combination of the receiver lines may be utilized. Additionally, the source may be activated at surface locations.

In the first embodiment of the invention, the source 15 is preferably conveyed into the survey wellbores 10 and moved to each of the source points 15$s_1$. This allows utilizing only one source for performing the survey. The source 15 preferably is adapted to transmit acoustic signals at any frequency within a range of frequencies. The control unit 70 is used to alter the amplitude and frequency of the acoustic signals transmitted by the source 15. Since the survey wellbore is strategically placed from relatively short distance from some or all of the producing formations, a relatively high frequency signals may be utilized to obtain high resolution seismic maps for short distances, which is nor feasible from any seismic surveys performed from the surface. Additionally, the source 15 may be oriented in any direction to transmit acoustic signals in a particular direction (herein referred to as the focused signals). This can allow obtaining true three dimensional bed boundary information respecting formations surrounding the survey wellbore 10. During drilling of the wellbore, core cuttings from known depths provide information about the rock structure, which in turn can be used to determine relatively accurately the acoustic velocities of some of the formations surrounding the survey wellbore 10. These velocities are utilized in processing the signals detected by the receiver lines, such as lines, such as line 12, 14 and 18. This provides more accurate delineation of bed boundaries compared to surface seismic surveys which typically use estimated values of acoustic velocities for subsurface formations.

The information obtained from the survey as described above is used to update preexisting seismic models. This may be done by combining the data obtained from the survey performed from the survey wellbore 10 or by any other known method. Additionally actual acoustic velocities of the subsurface formations obtained herein can be utilized to update the seismic models of the area.

Now referring to FIG 1a, the source line defined by $s_1$–$s_p$ is shown to be symmetrically placed in relation to the surface seismic lines $R_1$–$R_n$. It is preferred to utilize symmetrical receiver and transmitter configurations because it simplifies processing of data.

Figure 2:
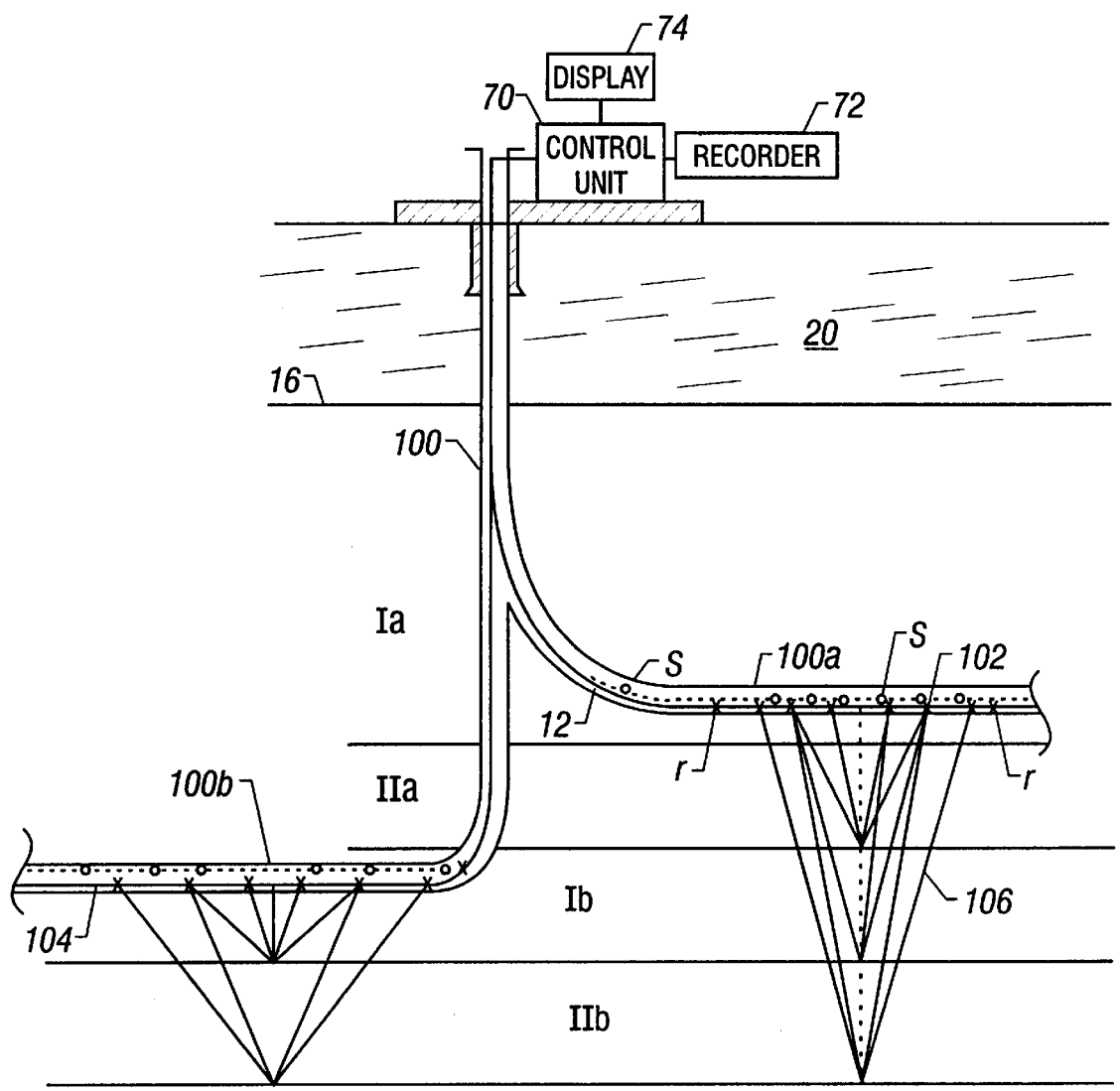
FIG. 2 shows a schematic illustration of the placement of a plurality of wellbores and corresponding transmitter and receivers for conducting subsurface seismic survey according to an embodiment of the present invention.

FIG. 2 shows a schematic illustration of the placement of a plurality of wellbores and corresponding transmitter and receiver lines for conducting subsurface seismic survey according to one method of one embodiment of the invention. In this configuration, a survey wellbore 100 is formed along a wellpath based on the prior seismic and other subsurface formation information available. The wellbore 100 has a first branch wellbore 100a placed above the first reservoir IIa and a second branch wellbore 100b placed above and along a second reservoir IIb. Other configurations for multiple survey wellbores may be adopted based upon the location of reservoirs to be developed. For example, separate wellbores may be drilled from different surface locations. A survey wellbore may be drilled along a dip to more precisely map the dipping formation utilizing relatively high frequency acoustic signals.

Each of the survey wellbores, such as wellbores 100a and 100b are lined with a receiver line 102 and 104 respectively. To conduct seismic survey from wellbore 100a, a transmitter is activated from each of the source points s. The reflected signals 106 are detected by the receivers r in the line 102, receivers in any other survey wellbore and by any other receivers placed on the surface. The data from the receivers is then processed by the control unit in the manner described earlier with respect to FIG. 1 to obtain information about the subsurface formations. Seismic data may be obtained at different frequencies and by utilizing focused signals in the manner described earlier with respect to FIG. 1.

Figure 3:
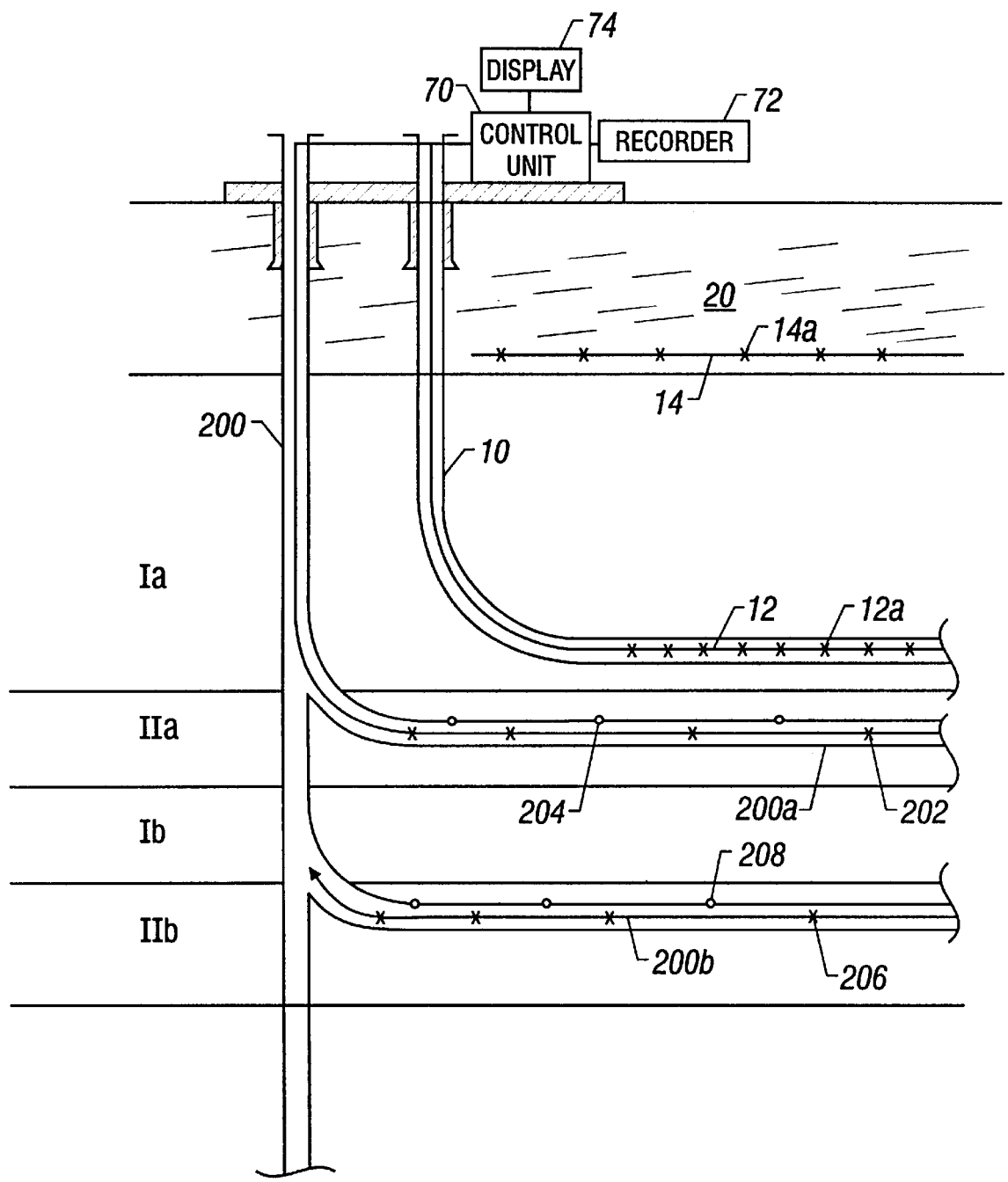
FIG. 3 shows a schematic illustration of multiple production wellbores formed for producing hydrocarbons utilizing the information obtained from surveys performed according to the present invention.

FIG. 3 shows a schematic illustration of multiple production wellbores formed for producing hydrocarbons utilizing the information obtained from surveys performed according to one embodiment of the invention. Once the subsurface geological information has been updated, the size and the placement of production wellbores, such as wellbores 100, 100a and 100b for developing a region are determined based upon the updated seismographs or subsurface models. The desired production wellbores are drilled and completed to produce hydrocarbons. It is desirable to place a plurality of receivers, such as receivers 202 in wellbore 200a and receivers 206 in wellbore 200b. In some cases it may be desirable to leave the receiver line 12 in the survey wellbore 10. During the life of the wellbores 200a and 200b, acoustic sources may be activated at selective locations in any of the production wellbores and in the survey wellbore 10. The receivers in the various wellbores detect signals corresponding to the transmitted signals. The detected signals are then processed to determine the condition of the various reservoirs over time. This information is then used to update reservoir models. The updated reservoir models are subsequently utilized to manage production from the various wellbores in the field. The updated models may be used to selectively alter production rates from any of the production wellbores in the field, to shut in a particular well, to workover a particular production wellbore, etc. The permanent availability of receiver lines in the survey wellbore 10, relatively close to the production wellbores 200a and 200b, provides more accurate information about the subsurface formations than surveys conducted from the surface. However, surface seismic surveys, if performed after the wellbores have been producing, may still be updated with information obtained from surveys performed using survey wellbore 10.

Figure 4:
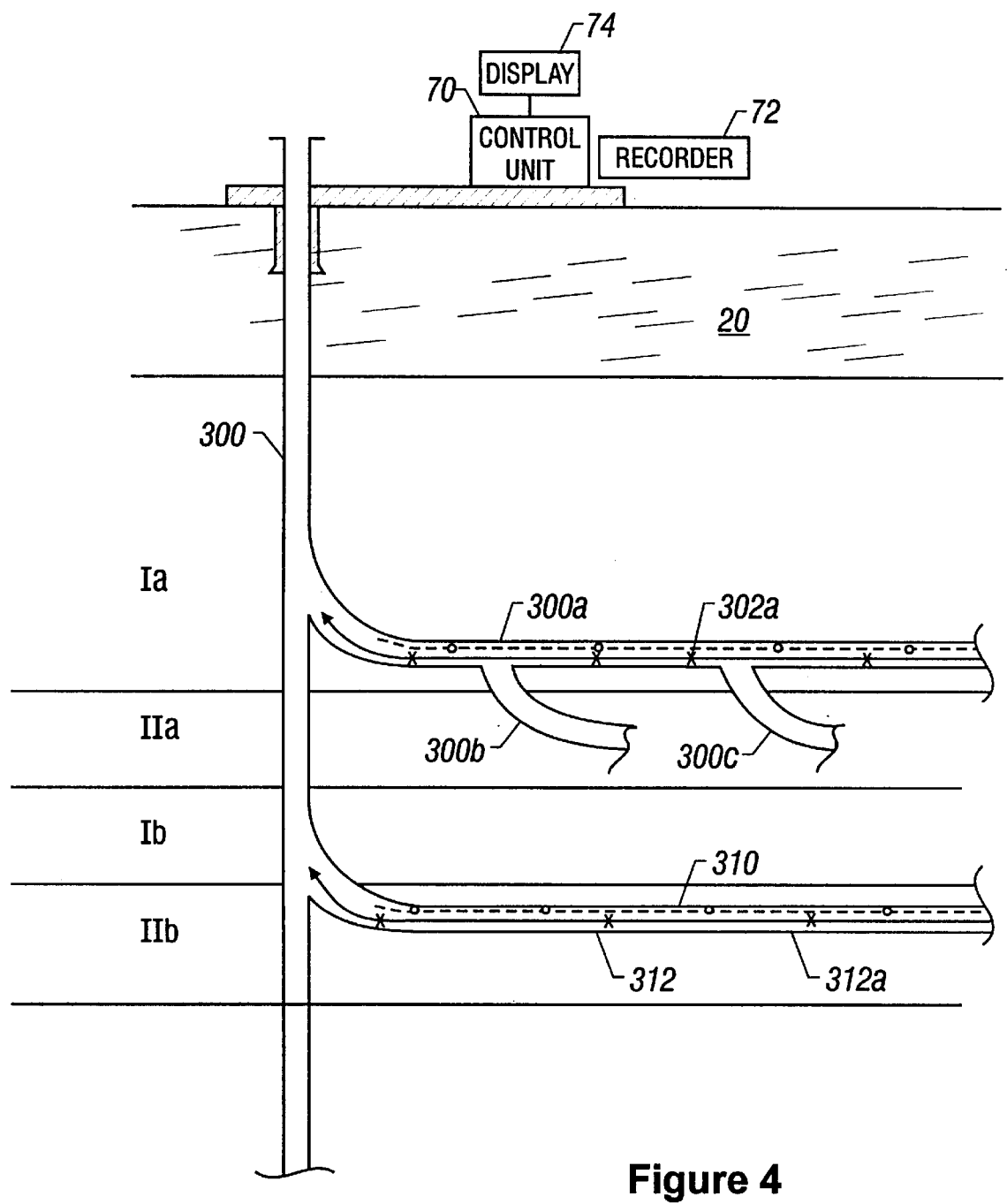
FIG. 4 shows a schematic illustration of multiple production wellbores formed for producing hydrocarbons utilizing the information obtained from surveys performed according to the present invention, wherein at least one of the production wellbores is formed from the wellbore formed for performing subsurface seismic survey.

FIG. 4 shows a schematic illustration of multiple production wellbores formed for producing hydrocarbons utilizing the information obtained from surveys performed according to one embodiment of the invention, wherein at least one of the production wellbores is formed from the wellbore formed for performing subsurface seismic survey. In some cases it may be desirable to drill a survey wellbore which can later be utilized to form production branch wellbores therefrom. FIG. 4 shows the formation of a survey wellbore 300a from a common vertical well section 300. The wellbore 300 is first used to perform seismic surveys in the manner described herein and then one or more production wellbores, such as wellbores 300b and 300c, are formed from the survey wellbore 300a. Additional production wellbores, such as wellbore 310 may be formed from the common wellbore section 300 or from other surface locations (not shown) as desired. Receivers 302a and 312a respectively shown in the wellbores 300a and 310 perform the same functions as explained earlier with respect to FIGS. 1–3.

Figure 5:
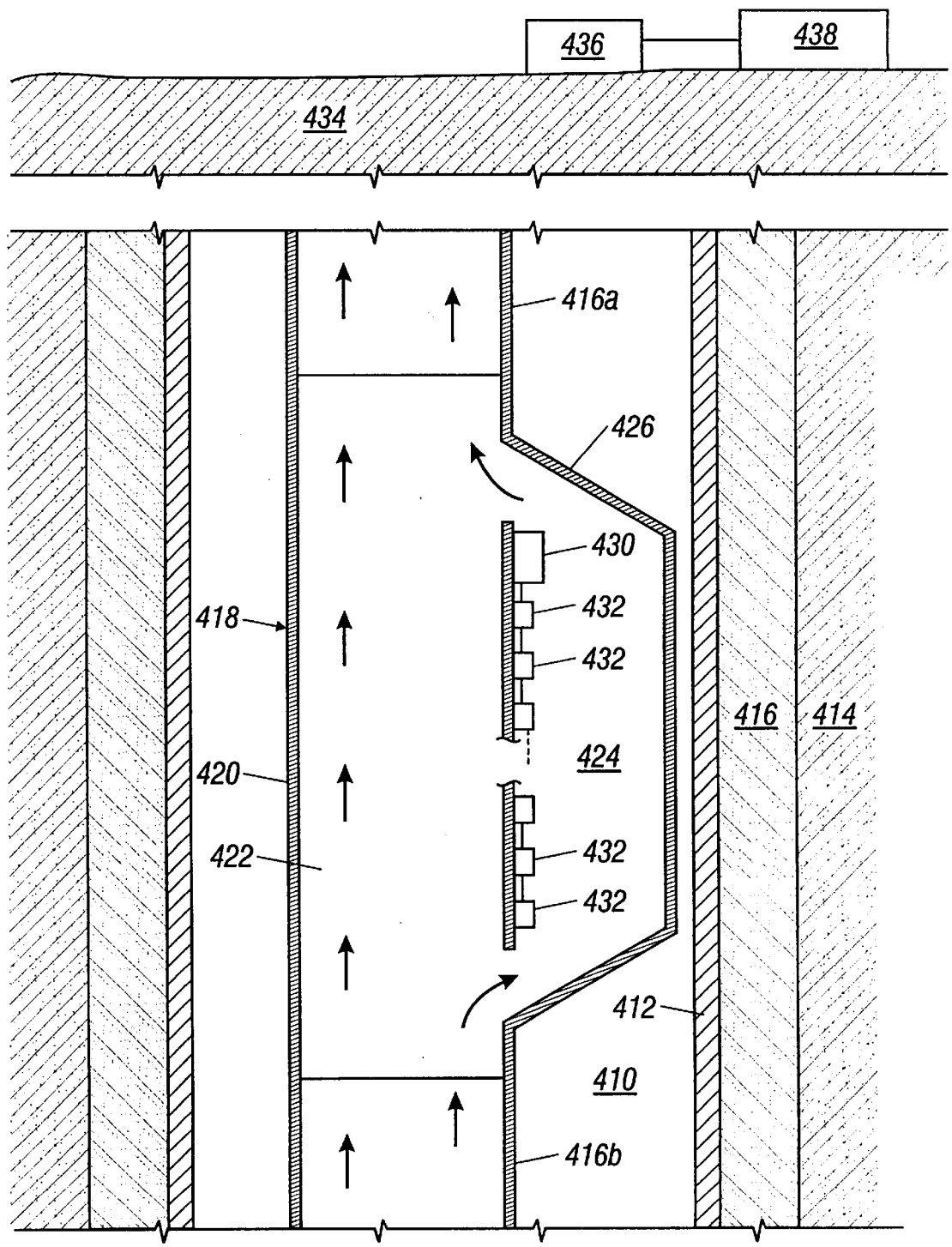
FIG. 5 is a diagrammatic view of an acoustic seismic monitoring system in accordance with the present invention.

Another aspect of the invention is the use of permanently installed downhole acoustic sensors. FIG. 5 depicts a schematic representation of the acoustic seismic monitoring system as described immediately above. FIG. 5 more particularly depicts a production well 410 for producing oil, gas or the like. Well 410 is defined by well casing 412 which is cemented or otherwise permanently positioned in earth 414 using an appropriate cement 416. Well 410 has been completed in a known manner using production tubing with an upper section of production tubing being shown at 416A and a lower section of production tubing being shown at 416B. Attached between production tubing 416A and 416B, at an appropriate location, is the permanent acoustic seismic sensor in accordance with the present invention which is shown generally at 418. Acoustic seismic sensor 418 comprises a housing 420 having a primary flow passageway 422 which communicates with and is generally in alignment with production tubing 416A and 416B. Housing 420 also includes a side passageway 424 which is laterally displaced from primary flow passageway 422. Side passageway 424 is defined by a laterally extending section 426 of housing 420 and an interior dividing wall 428. Positioned within side passageway 424 is a downhole electronics and control module 430 which is connected in series to a plurality of permanent acoustic receivers 432 (e.g., hydrophones, seismometers and accelerometers). The acoustic receivers 432 are placed longitudinally along production tubing 416 (and therefore longitudinally along the wall of the borehole) in a region of the geological formation which is of interest in terms of sensing and recording seismic changes with respect to time. At the surface 434 is a surface control system 436 which controls an acoustic transmitter 438. As discussed, transmitter 438 may also be located beneath the surface 434. Transmitter 438 will periodically transmit acoustic signals into the geological formation which are then sensed by the array of acoustic receivers 432 with the resultant sensed data being processed using known analysis techniques.

A more complete description of wellbores containing permanent downhole formation evaluation sensors can be found in U.S. Pat. No. 5,662,165 all of the contents of which are incorporated herein by reference.

As discussed in trade journals such as in the articles entitled "4D Seismic Helps Track Drainage, Pressure Compartmentalization," Oil and Gas Journal, Mar. 27, 1995, pp 55–58, and "Method Described for Using 4D Seismic to Track Reservoir Fluid Movement," Oil and Gas Journal, Apr. 3, 1995, pp. 70–74 (both articles being fully incorporated herein by reference), seismic monitoring of wells over time is becoming an important tool in analyzing and predicting well production and performance. Prior to the present invention, such seismic monitoring could only be done in near real time using known wire-line techniques; or on sensors mounted on the outside of tubing of various sorts for shallow applications (never in producing wells). Examples of such seismic monitoring are described in U.S. Pat. No. 5,194,590; the article "Time-lapse crosswell seismic tomogram Interpretation: Implications for heavy oil reservoir characterization, thermal recovery process monitoring and tomographic imaging technology" Geophysics v. 60, No. 3, (May–June), p 631–650; and the article "Crosswell seismic radial survey tomograms and the 3-D interpretation of a heavy oil steamflood." Geophysics v. 60, no. 3, (May–June) p 651–659 all of the contents of which are incorporated herein by reference. However, in accordance with the present invention, a significant advance in seismic monitoring is accomplished by installing the seismic (e.g., acoustic) sensors as a permanent downhole installation in a well. A plurality of seismic transmitters, as described in U.S. Pat. No 5,662,165 are used as sources of seismic energy at boreholes at known locations. The seismic waves detected at receivers in other boreholes, upon proper analysis, provide a detailed three dimensional picture of a formation and fluids in the formation with respect to time. Thus, in accordance with this invention, a well operator has a continuous real time three dimensional image of the borehole and surrounding formation and is able to compare that real time image with prior images to ascertain changes in the formation; and as discussed in detail above, this constant monitoring can be done from a remote location.

Such an imaging of fluid conditions is used to control production operations in the reservoir. For example, an image of the gas-water contact in a producing gas reservoir makes it possible to take remedial action before water is produced in a well by selectively closing sleeves, packers, safety valves, plugs and any other fluid control device downhole where it is feared that water might be produced without remedial action. In a steam-flood or $CO_2$ flood operation for secondary recovery of hydrocarbons, steam or $CO_2$ are injected into the reservoir at selected injection wells. The steam or $CO_2$ drive the oil in the pore spaces of the reservoir towards the producing wells. In secondary recovery operations, it is critical that the steam or $CO_2$ not enter the producing wells: if a direct flow path for steam or $CO_2$ is established between the injection well and the recovery well (called a breakthrough), further "flushing" operations to recover oil are ineffective. Monitoring of the position of the steam/oil or $CO_2$/oil interface is therefore important and by closing sleeves, packers, safety valves, plugs and any other fluid control device in a producing well where breakthrough is imminent, the flow patterns can be altered sufficiently to avoid a breakthrough. In addition, sleeves and fluid pressure control devices can be operated in the injection wells to affect the overall flow of fluids in the reservoir. The downhole seismic data for performing the tomographic analysis is transmitted uphole using methods described in U.S. Pat. No 5,662,165, gathered by the control center and transmitted to a remote site where a powerful digital computer is used to perform the tomographic analysis in accordance with methods described in the patent and references above.

Another aspect of the invention is the ability to control a fracturing operation. In a "frac job", fluid at a high pressure is injected into a geologic formation that lacks adequate permeability for the flow of hydrocarbons. The injection of high pressure fluid into a formation at a well has the effect of fracturing the formation. These fractures generally propagate away from the well in directions determined by the properties of the rock and the underground stress conditions. As discussed by P. B. Wills et al in an article entitled "Active and Passive Imaging of Hydraulic fractures" *Geophysics, the Leading Edge of Exploration*, July, p 15–22, (incorporated herein by reference), the use of downhole geophones in one well (a monitor well) makes it possible to monitor the propagation of fractures from another well in which fracturing is being induced. The propagating fracture in the formation acts as a series of small seismic sources that emit seismic waves. These waves can be recorded in the sensors in the monitor well and based upon the recorded signals in a number of monitor wells, the active edge of the fracture can be mapped. Having such real-time observations makes it possible to control the fracturing operation itself using the methods of this invention.

While the foregoing disclosure is directed to the preferred embodiments of the invention various modifications will be apparent to those skilled in the art. It is intended that all variations within the scope and spirit of the appended claims be embraced by the foregoing disclosure. Examples of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto.

What is claimed is:

1. A method of recovering hydrocarbons from a production wellbore producing hydrocarbons from a formation comprising:
    (a) injecting a fluid in an injection wellbore spaced apart from the production wellbore to make a fluid/hydrocarbon interface in the formation;
    (b) permanently installing a plurality of seismic sensors in a survey wellbore;
    (c) transmitting seismic signals into the formation from a plurality of source locations;
    (d) detecting said seismic signals by the seismic sensors in the survey wellbore;
    (e) determining a parameter of interest relating to the fluid/hydrocarbon interface from the detected seismic signals; and
    (f) operating a downhole tool at at least one location selected from (i) the production wellbore, and, (ii) the injection well, in response to the determined parameter of interest to control the flow of hydrocarbons into the production wellbore.

2. The method of claim 1 wherein the downhole tool is selected from a group consisting of flow control devices and formation isolation tools.

3. The method of claim 1 wherein the survey wellbore is the production wellbore.

4. The method of claim 1 wherein the plurality of source locations includes at least one location in the injection wellbore.

5. The method of claim 1 wherein the fluid being injected is selected from the group consisting of steam, water and gas.

6. The method of claim 1 wherein the hydrocarbons comprise a gas and the fluid is water.

7. The method of claim 6 wherein the parameter of interest is a location of the gas-fluid interface.

8. The method of claim 1 wherein the hydrocarbons comprise oil and the fluid is selected from the group consisting of (A) water, (B) steam, (C) $CO_2$, and, (D) gas.

9. The method of claim 1 wherein determining said parameter of interest further comprises updating a model of a reservoir in the formation producing said hydrocarbons.

10. The method of claim 1 wherein the survey wellbore is a side well.

11. The method of claim 1 wherein said seismic signals are transmitted at a location selected from (A) a wellbore, and, (B) the surface of the earth.

12. A method of recovering hydrocarbons from a production wellbore producing hydrocarbons from a formation comprising:
    (a) injecting a fluid in an injection wellbore spaced apart from the production wellbore to make a fluid/hydrocarbon interface in the formation;
    (b) permanently installing a plurality of seismic sensors within production tubing in the production wellbore;
    (c) transmitting seismic signals into the formation from a plurality of source locations;
    (d) detecting said seismic signals by the seismic sensors in the production wellbore;
    (e) determining a parameter of interest relating to the fluid/hydrocarbon interface from the detected seismic signals; and (f) operating a downhole tool at at least one location selected from (i) the production wellbore, and, (ii) the injection well, in response to the determined parameter of interest to control the flow of hydrocarbons into the production wellbore.

13. The method of claim 12 wherein the downhole tool is selected from a group consisting of flow control devices and formation isolation tools.

14. The method of claim 12 wherein the plurality of source locations includes at least one location in the injection wellbore.

15. The method of claim 12 wherein the fluid being injected is selected from the group consisting of steam, water and gas.

16. The method of claim 12 wherein the seismic sensor is selected from the group consisting of geophone, accelerometer, hydrophone and fiber optic sensor.

17. The method of claim 12 wherein the hydrocarbons comprise a gas and the fluid is water.

18. The method of claim 17 wherein the parameter of interest is a location of the gas-fluid interface.

19. The method of claim 12 wherein the hydrocarbons comprise oil and the fluid is selected from the group consisting of (A) water, (B) steam, (C) $CO_2$, and, (D) gas.

20. The method of claim 12 wherein determining said parameter of interest further comprises updating a model of a reservoir in the formation producing said hydrocarbons.

21. The method of claim 12 wherein the survey wellbore is a side well.

22. The method of claim 12 wherein said seismic signals are transmitted at a location selected from (A) a wellbore, and, (B) the surface of the earth.

* * * * *